United States Patent [19]

Spindler et al.

[11] Patent Number: 4,994,615

[45] Date of Patent: Feb. 19, 1991

[54] PROCESS FOR THE PREPARATION OF OPTICALLY ACTIVE SECONDARY ARYLAMINES

[75] Inventors: Felix Spindler, Starrkirch-Wil; Benoit Pugin, Münchenstein, both of Switzerland

[73] Assignee: Ciba-Geigy Corporation, Ardsley, N.Y.

[21] Appl. No.: 79,054

[22] Filed: Jul. 29, 1987

[30] Foreign Application Priority Data

Aug. 4, 1986 [CH] Switzerland ................. 3116/86

[51] Int. Cl.$^5$ .............................................. C07C 57/00
[52] U.S. Cl. .................................. 564/304; 544/159; 544/299; 546/329; 548/490; 548/557; 549/72; 549/480; 564/302
[58] Field of Search ............... 564/302, 303, 304; 508/13; 544/159, 299; 548/490; 549/72

[56] References Cited

U.S. PATENT DOCUMENTS

| | | | |
|---|---|---|---|
| 2,608,583 | 8/1952 | Aschner | 564/302 |
| 3,849,480 | 11/1974 | Knowles et al. | 564/302 X |
| 3,883,580 | 5/1975 | Solodar | 564/302 X |
| 3,968,147 | 7/1976 | Solodar | 564/302 X |
| 4,187,313 | 2/1980 | Gschwend et al. | 564/304 X |
| 4,556,740 | 12/1985 | Hansen et al. | 568/13 |

FOREIGN PATENT DOCUMENTS 0104375  1984  European Pat. Off.

OTHER PUBLICATIONS

H. B. Kagan, Chiral Ligands for Asymmetric Catalysis, Asymmetric Synthesis, vol. 5, pp. 13–23 (1985).
R. Uson et al, Inorg. Chem. Acta 73, p. 275 et seq. (1983).
S. Brunie et al., Journal of Organometallic Chemistry, 114 (1976), pp. 225–235.
M. Green et al., J. Chem. Soc. (A), pp. 2334 et seq. (1971).

*Primary Examiner*—Robert V. Hines
*Attorney, Agent, or Firm*—Stephen V. O'Brien

[57] ABSTRACT

Asymmetric hydrogenation of prochiral N-arylketimines to give optically active secondary amines at a temperature of $-20°$ to $80°$ C., a hydrogen pressure of $10^5$ to $6.10^6$ Pa with the addition of catalytic amounts of an iridium compound of the formula III or IIIa $$[XIrYZ] \qquad (III)$$

or $$[XIrY^{\oplus}A^{\ominus}] \qquad (IIIa)$$

in which X is two olefin ligands or one diene ligand, Y is a chiral diphosphine, the secondary phosphine groups of which are linked by 2-4 C atoms and which, together with the Ir atom, forms a 5-, or 6- or 7-ring, or Y is a chiral diphosphinite, the phosphinite groups of which are linked via 2 C atoms and which together with the Ir atom forms a 7-ring, Z is Cl, Br or I and $A^{63}$ is the anion of an oxygen acid or complex acid, and if appropriate with the addition of an ammonium or alkali metal chloride, bromide or iodide.

13 Claims, No Drawings

PROCESS FOR THE PREPARATION OF OPTICALLY ACTIVE SECONDARY ARYLAMINES

The present invention relates to a process for the preparation of optically active secondary amines by asymmetric hydrogenation of prochiral N-arylketimines with chiral iridium diphosphine or diphosphinite complexes.

European Patent A-No. 0,104,375 describes chiral diphosphine ligands, complexes of which with metals of group VIII of the periodic table can be used as catalysts for asymmetric hydrogenation of α-(acylamine)-acrylic acids.

It has been found that iridium compounds with chiral diphosphine or diphosphinite ligands are suitable homogeneous asymmetric catalysts for the hydrogenation of prochiral N-arylketimines. This reaction leads to optically active secondary N-arylamines with high chemical conversions and good optical yields. Optically active means an excess of one enantiomer with the R- or S-configuration.

The present invention relates to a process for the preparation of optically active secondary N-arylamines of the formula I

in which $R^1$ is $C_6$–$C_{12}$-aryl or $C_4$–$C_{11}$-heteroaryl which has 1 or 2 heteroatoms in the ring and is bonded via a ring C atom, it being possible for these radicals to be substituted by $C_1$–$C_{12}$-alkyl, $C_1$–$C_{12}$-alkoxy, $C_1$–$C_{12}$-alkylthio, $C_1$–$C_6$-haloalkyl, halogen, —OH, —CN, $C_6$–$C_{12}$-aryl or -aryloxy or -arylthio, $C_7$–$C_{16}$-aralkyl or -aralkoxy or -aralkylthio, it being possible for the aryl radicals in turn to be substituted by $C_1$–$C_4$-alkyl, -alkoxy, -alkylthio, halogen, —OH, —CN, —CONR$^4$R$^5$ or -COOR$^4$, secondary amino with 2 to 24 C atoms,

or —COOR$^4$, in which $R^4$ and $R^5$ independently of one another are $C_1$–$C_{12}$-alkyl, phenyl or benzyl or $R^4$ and $R^5$ together are tetra- or pentamethylene or 3-oxapentylene; $R^2$ and $R^3$ differ from one another and are $C_1$–$C_{12}$-alkyl or cycloalkyl with 3–8 ring C atoms, which are unsubstituted or substituted by —OH, —CN, halogen, $C_1$–$C_{12}$-alkoxy, phenoxy, benzyloxy, secondary amino with 2 to 24 C atoms,

or —COOR$^4$, $C_6$–$C_{12}$-aryl or $C_7$–$C_{16}$-aralkyl which is unsubstituted or substituted in the same way as $R^1$, —CONR$^4$R$^5$ or —COOR$^4$, in which $R^4$ and $R^5$ are as defined above; or $R^1$ is as defined above and $R^2$ and $R^3$ together are alkylene which has 2 to 5 C atoms and is uninterrupted or interrupted by 1 or 2 —O—, —S— or —NR$^4$— and/or is unsubstituted or substituted by =O or as described above for $R^2$ and $R^3$ alkyl, and/or is fused with benzene, furan, thiophene or pyrrole, or $R^2$ is as defined above, $R^1$ is bounded to $R^3$ and are alkylene which has 2 to 5 C atoms and is uninterrupted or interrupted by 1 or 2 —O—, —S— or —NR$^4$— and/or unsubstituted or substituted by =O or as described above for alkyl $R^2$ and $R^3$, and/or is fused to benzene, furan, thiophene or pyrrole, and * is chiefly the R- or S-configuration, by asymmetrically catalyzed hydrogenation of N-arylated prochiral ketimines of the formula II

in which $R^1$, $R^2$ and $R^3$ are as defined above, in the presence of complex salts of a noble metal with chiral ligands, which comprises carrying out the hydrogenation at a temperature of −20° to 80° C. under as hydrogen pressure of $10^5$ Pa to $6.10^6$ Pa and adding to the reaction mixture catalytic amounts of an iridium compound of the formula III or IIIa

or

in which X is two olefin ligands or one diene ligand, Y is a chiral diphosphine, the secondary phosphine groups of which are linked by 2–4 C atoms and which, together with the Ir atom, forms a 5-, 6- or 7-ring, or Y is a chiral diphosphinite, the phosphinite groups of which are linked via 2 C atoms and which together with the Ir atom forms a 7-ring, Z is Cl, Br or I and A⊖ is the anion of an oxygen acid or complex acid.

$R^1$ can be substituted in any desired positions by identical or different radicals, for example with 1 to 5, preferably 1 to 3, substituents. The substitution in the two ortho-positions relative to the N atom may have a favourable influence on the desired yields, and in this case $R^2$ is preferably not aryl. The two ortho-positions are preferably substituted, in particular by $C_1$–$C_{12}$-alkyl.

Suitable substituents for aryl and aralkyl $R^1$, $R^2$ and $R^3$ are: $C_1$–$C_{12}$-, preferably $C_1$–$C_6$- and in particular $C_1$–$C_4$-alkyl, -alkoxy or -alkylthio, for example methyl, ethyl, propyl, n-, i- and t-butyl, the isomers of pentyl, hexyl, octyl, nonyl, decyl, undecyl and dodecyl and corresponding alkoxy and alkylthio radicals; $C_1$–$C_6$-, preferably $C_1$–$C_4$-haloalkyl with preferably F and Cl as halogen, for example trifluoro- or trichloromethyl, difluorochloromethyl, fluorodichloromethyl, 1,1-difluoroeth-1-yl, 1,1-dichloroeth-1-yl, 1,1,1-trichloro- or -trifluoroeth-2-yl, pentachloroethyl, pentafluoroethyl, 1,1,1-trifluoro-2,2-dichloroethyl, n-perfluoropropyl, i-perfluoropropyl, n-perfluorobutyl, fluoro- or chloromethyl, difluoro- or dichloromethyl, 1-fluoro- or -chloro-eth-2-yl or -eth-1-yl, 1-, 2- or 3- fluoro- or -chloro-prop-1-yl or -prop-2-yl or -prop-3-yl, 1-fluoro-or-chloro-but-1-yl, -but-2-yl, -but-3-yl or-but-4-yl, 2,3-dichloro-prop-1-yl, 1-chloro-2-fluoro-prop-3-yl and 2,3-dichloro-but-1-yl; halogen, preferably F and Cl; $C_6$–$C_{12}$-aryl, -aryloxy or -arylthio, in which aryl is preferably naphthyl or, in particular, phenyl, $C_7$–$C_{16}$-aralkyl, -aralkoxy and -aralkylthio, in which the aryl radical is preferably naphthyl or, in particular, phenyl and the alkylene radical is linear or branched and contains 1 to 10, preferably 1 to 6 and in particular 1-3 C atoms, for example benzyl, naphthylmethyl, 1- or 2-phenyleth-1-yl or -eth-2-yl or 1-, 2- or 3-phenyl-prop-1-yl, -prop-2-yl or -prop-3-yl, benzyl being particularly preferred; the abovementioned radicals containing aryl groups can in turn be mono- or polysubstituted, for example by $C_1$-$C_4$-alkyl, -alkoxy or -alkylthio, halogen, —OH, —CN, —$CONR^4R^5$ or —$COOR^4$, $R^4$ and $R^5$ being as defined above; examples are methyl, ethyl, n- and i-propyl, butyl, corresponding alkoxy and alkylthio radicals, F, Cl, Br, dimethyl-, methylethyl- and diethylcarbamoyl and methoxy-, ethoxy-, phenoxy- and benzyloxycarbonyl, secondary amino with 2 to 24, preferably 2 to 12 and in particular 2 to 6 C atoms, the secondary amino preferably containing 2 alkyl groups, for example dimethyl-, methylethyl-, diethyl-, methylpropyl-, methyl-n-butyl-, di-n-propyl-, di-n-butyl and di-n-hexylamino; —$CONR^4R^5$, in which $R^4$ and $R^5$ independently of one another are $C_1$-$C_{12}$-, preferably $C_1$-$C_6$- and in particular $C_1$-$C_4$-alkyl, or $R^4$ and $R^5$ together are tetra- or pentamethylene or 3-oxapentylene, it being possible for the alkyl to be linear or branched, for example dimethyl-, methylethyl-, diethyl-, methyl-n-propyl-, ethyl-n-propyl-, di-n-propyl-, methyl-n-butyl-, ethyl-n-butyl-, n-propyl-n-butyl- and di-n-butylcarbamoyl; -$COOR^4$, in which $R^4$ is $C_1$-$C_{12}$-, preferably $C_1$-$C_6$-alkyl, which can be linear or branched, for example methyl, ethyl, n- and i-propyl, n-, i-and t-butyl, and the isomers of pentyl, hexyl, heptyl, octyl, nonyl, decyl, undecyl and dodecyl.

Aryl $R^1$ is preferably unsubstituted or substituted naphthyl or, in particular, phenyl. Heteroaryl $R^1$ is preferable a 5- or 6- membered ring with 1 or 2 identical or different heteroatoms, in particular O, S or N, which preferably contains 4 or 5 C atoms and can be fused with benzene. Examples of heteroaromatics from which $R^1$ can be derived are furan, pyrrole, thiophene, pyridine, pyrimidine, indole and quinoline.

The substituents of $R^2$ and $R^3$ have the same preferred meanings as the substituents of $R^1$. Alkyl $R^2$ and $R^3$ is preferably unsubstituted or substituted $C_1$-$C_6$-, in particular $C_1$-$C_4$-alkyl, which can be linear or branched. Examples are methyl, ethyl, i- and n-propyl, i-, n- and t-butyl, and the isomers of pentyl, hexyl, heptyl, octyl, nonyl, decyl, undecyl and dodecyl.

Unsubstituted or substituted cycloalkyl $R^2$ and $R^3$ preferably contains 3 to 6, in particular 5 or 6, ring C atoms. Examples are cyclopropyl, cyclobutyl, cyclopentyl, cyclohexyl, cycloheptyl and cyclooctyl.

Aryl $R^2$ and $R^3$ is preferably unsubstituted or substituted naphthyl or, in particular, phenyl. Aralkyl $R^2$ and $R^3$ is preferably unsubstituted or substituted phenylalkyl with 1-10, preferably 1 to 6 and in particular 1 to 4 C atoms in the alkylene, it being possible for the alkylene to be linear or branched. Examples are, in particular, benzyl, and 1-phenyleth-1-yl, 2-phenyleth-1-yl, 1-phenylprop-1-yl, 1-phenylprop-2-yl, 1-phenylprop-3-yl, 2-phenylprop-1yl, 2-phenylprop-2-yl and 1-phenylbut-4-yl.

$R^4$ and $R^5$ in — $CONR^4R^5$ and —$COOR4$ $R^2$ and $R^3$ are preferably $C_1$-$C_6$, in particular $C_1$-$C_4$-alkyl, or $R^4$ and $R^5$ together are tetramethylene, pentamethylene or 3-oxapentylene. Examples of alkyl have been mentioned above.

Alkylene $R^2$ and $R^3$ together or $R^1$ bounded to $R^3$ is preferably interrupted by 1 —O—, —S— or —$NR^4$—, preferably —O—. $R^2$ and $R^3$ or $R^1$ bounded to $R^3$, together with the C atom or the —N=C-group to which they are bonded preferably form a 5- or 6-membered ring. The substituents have the abovementioned preferred meanings. Fused alkylene $R^2$ and $R^3$ or $R^1$ bonded to $R^3$ is preferably alkylene fused with benzene or pyridine. Examples of alkylene are: ethylene, 1,2- or 1,3-propylene, 1,2-, 1,3- or 1,4-butylene, 1,5pentylene and 1,6-hexylene. Examples of alkylene which is interrupted or substituted by =O are 2-oxa-1,3-propylene, 2-oxa-1,4-butylene, 2-oxa- or 3-oxa-1,5-pentylene, 3-thia-1,5-pentylene, 2-thia-1,3-propylene, 2-methylimino-1,3propylene, 2-ethylimino-1,4-butylene, 2- or 3-methylimino-1,5-pentylene, 1-oxo-2-oxa-1,3-propylene, 1-oxo-2-oxa-1,4-butylene, 2-oxo-3-oxa-1,4-butylene and 1-oxa-2-oxo-1,5-pentylene. Examples of fused alkylene are:

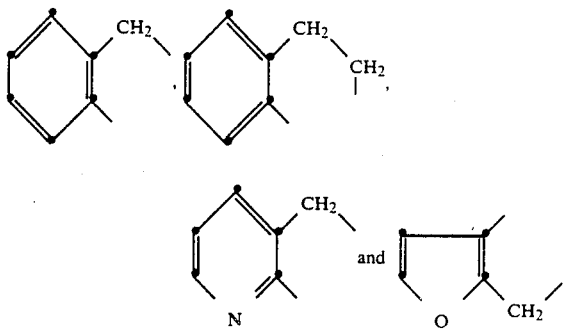

Examples of fused and interrupted alkylene which is unsubstituted or substituted by =O are

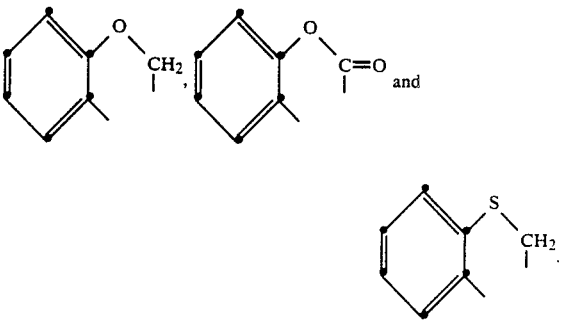

In a preferred group, in formula II $R^1$ is 2,6-dimethylphen-1-yl or 2-methyl-6-ethylphen-1-yl, $R^2$ is methyl and $R^3$ is methoxymethyl.

N-Arylimines of the formula II are known or can be prepared from ketones and arylamines by known processes. In one embodiment of the process, the N-arylimines of the formula II can also be prepared in situ from the corresponding ketones and arylamines.

The process is preferably carried out at a temperature of $-20°$ to $50°$ C., in particular $-20°$ to $20°$ C. and especially $-20°$ to $10°$ C., and preferably under a hydrogen pressure of $2.10^5$ to $3.10^6$ Pa, in particular $8.10^5$ to $3.10^6$ Pa.

In the formulae III and IIIa, an olefin ligand X can be, for example, butene, propene or, in particular, ethylene, and the diene ligand is preferably an open-chain or cyclic diene, the diene groups of which are linked by one or two C atoms. The diene is preferably hexadiene, cyclooctadiene or norbornadiene.

In the chiral diphosphine, the phosphine groups are preferably linked via an aliphatic group with 2-4 C atoms which can be substituted by $C_1$-$C_4$-alkyl, $C_5$- or $C_6$-cycloalkyl, phenyl or benzyl. The aliphatic group can be alkylene or a cycloaliphatic group with 5 or 6 ring C atoms, or an aliphatic-heterocyclic group with 1 or 2 —O— or =N—$C_1$-$C_{12}$-alkyl or -acyl or -aminocarbonyl, -phenyl or -benzyl and 3–5 C. atoms in the ring. The rings can be substituted by $C_1$-$C_4$-alkyl, $C_5$-$C_7$-cycloalkyl, phenyl or benzyl.

Y in the formulae III or IIIa is preferably a chiral diphosphine, the phosphine groups of which are linked by 4 C atoms and which, together with the Ir atom, forms a 7-ring.

The phosphine groups and phosphinite groups preferably contain $C_1$-$C_{12}$-alkyl, cycloalkyl which has 5 to 8 ring C atoms and can be substituted by 1 to 3 $C_1$-$C_6$-alkyl groups, phenyl, $C_7$-$C_{12}$-phenylalkyl or alkylphenylalkyl with 1 to 6 C atoms in the alkyl groups and 1 to 5 C atoms in the alkylene group. t-Butyl, phenyl, benzyl and cyclohexyl are particularly preferred. Suitable chiral diphosphines are described in H. B. Kagan, Chiral Ligands for Asymmetric Catalysis, Asymmetric Synthesis, Volume 5, pages 13 –23, Academic Press, Inc., N.Y. (1985).

Examples are (Ph is phenyl):

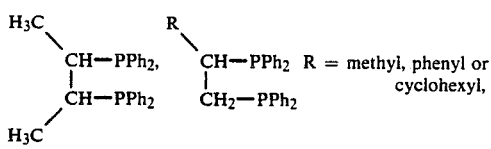

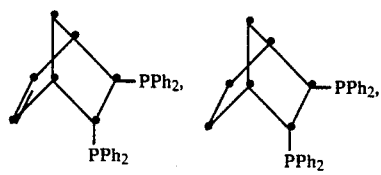

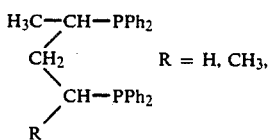

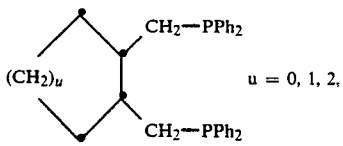

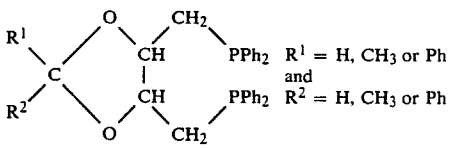

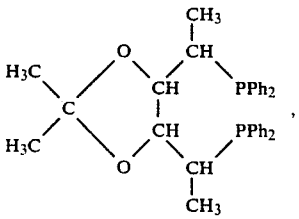

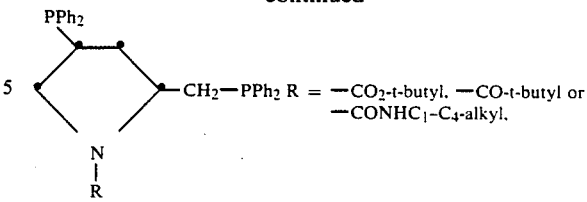

and

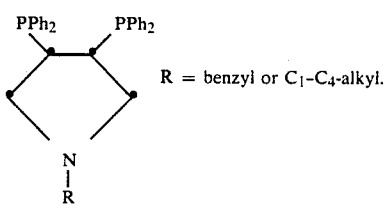

An example of diphosphinites is 1-0-phenyl-4,6-0-(R)-benzylidene-2,3-0-bis(diphenylphosphino)-β-D-glucopyranoside of the formula

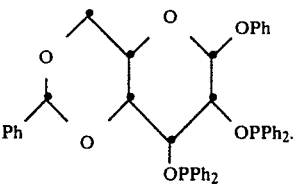

In formula III, Z is preferably Cl or Br. A⊖ in formula IIIa is preferably $ClO_4^\ominus$, $CF_3SO_3^\ominus$, $BF_4^\ominus$, $B(phenyl)_4^\ominus$, $PF_6^\ominus$, $SbCl_6^\ominus$, $AsF_6^\ominus$ or $SbF_6^\ominus$.

A preferred group of iridium compounds are those of III in which X is cyclooctadiene, Z is Cl and Y is (R)— or (S)—

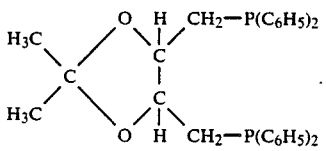

The iridium compounds of the formulae III and IIIa are known or can be prepared by known processes, see, for example, R. Uson et al., Inorg. Chim. Acta 73, page 275 et seq. (1983); S. Brunie et al., Journal of Organometallic Chemistry, 114 (1976), pages 225–235 and M. Green et al., J. Chem. Soc. (A), pages 2334 et seq. (1971).

The iridium compounds can be used as isolated compounds. It is advantageous to prepare the compounds in situ and to use them directly.

The iridium compounds are preferably used in amounts of 0.01 to 5, in particular 0.05 to 2 mol %, based on the compounds of the formula II.

A preferred process procedure comprises additionally using an ammonium or alkali metal chloride, bromide or iodide. The addition of chlorides, bromides or iodides is particularly advantageous if compounds of the formula IIIa are used as catalysts. The chlorides, bromides and iodides are preferably used in amounts of 0.01 to 100, in particular 0.05 to 50 mol %, based on the compounds of the formula II. Preferred salts are the iodides. Ammonium is preferably tetraalkylammonium with 1 to 6 C atoms in the alkyl groups, and the alkali metal is preferably sodium, lithium or potassium.

The reaction can be carried out in the absence or presence of solvents. Suitable solvents, which can be used by themselves or as a mixture of solvents, are, for example: aliphatic and aromatic hydrocarbons, for example pentane, hexane, cyclohexane, methylcyclohexane, benzene, toluene and xylene; alcohols, such as, for example, methanol, ethanol, propanol and butanol; ethers, such as, for example, diethyl ether, diethylene glycol dimethyl ether, tetrahydrofuran and dioxane; halogenohydrocarbons, for example methylene chloride, chloroform, 1,1,2,2-tetrachloroethane and chlorobenzene; esters and lactones, for example ethyl acetate, butyrolactone and valerolactone; and acid amides and lactams, for example dimethylformamide, dimethylacetamide and N-methylpyrrolidone.

The compounds of the formula I are biologically active substances or intermediates for the preparation of such substances with an N-aryl-secondary amine group, in particular in the pharmaceuticals and agrochemicals sector. Thus, for example, o,o-dialkylarylketamine derivatives, in particular those with alkyl and/or alkoxyalkyl groups, act as fungicides, in particular as herbicides. The derivatives can be amine salts, acid amides, for example of chloroacetic acid, tertiary amines and ammonium salts (see, for example, European Patent A-No. 0,077,755 and European Patent A-0,115,470).

The following examples illustrate the invention in more detail.

EXAMPLES 1-10: p 160 mmol of N(2,6-dimethylphen-1-yl)-methoxymethylmethylketimine are introduced into a 250 ml two-necked flask under an $N_2$ inert gas atmosphere. The flask is evacuated to $5 \times 10^3$ Pa and flushed with nitrogen. Thereafter, 30 ml each of methanol and benzene are added and the mixture is stirred at room temperature for 2 minutes (solution A).

10 ml each of methanol and benzene are introduced into a 50 ml two-necked flask under an $N_2$ inert gas atmosphere. Thereafter, $4.10^{-}$mol of [Ir(cyclooctadiene)Cl]$_2$, $8.8 \times 10^{-5}$ mol of diphosphine and $1.2 \times 10^{-3}$ mol of tetrabutylammonium iodide (only in the case of Example 1 and 2) are added in succession. After each addition, the mixture is stirred until a homogeneous solution is present (solution B).

Solutions A and B are introduced in succession into a 0.3 l steel autoclave with a capillary with exclusion of air. $2 \times 10^6$ Pa of hydrogen are forced in through a gas inlet valve. At the same time, $1.4 \times 10^7$ Pa of hydrogen are forced into a 100 ml reservoir. The temperature is 20-22° C. The reaction is carried out under a constant pressure of hydrogen of $2 \times 10^6$ Pa until no further uptake of hydrogen takes place. The reaction mixture is then flushed into a 250 ml flask with nitrogen.

The solvent is removed at 80° C. on a rotary evaporator. A crude product is obtained and is distilled under a high vacuum (1-10 Pa). The optical yield is then determined by polarometry (A. F. Lee et al., J. Chem. Arc. 1954, 145) or by means of $^1$H-NMR, using shift reagents.

In Example 2, 80 mmol of ketimine are used. In the remaining examples, the catalyst concentration is 1 mol % (40 mmol), 20 ml of solvent being used. The reactions are carried out in a 120 ml glass or 65 ml steel autoclave.

The optical yields (ee in %), reaction times, conversion, solvents and reaction temperatures are shown in Table 1.

TABLE 1

| Example | Diphosphine | Temperature (°C) | Solvent | Reaction time (hours) | Conversion (%) | Optical yield % ee (configuration) |
|---|---|---|---|---|---|---|
| 1 | 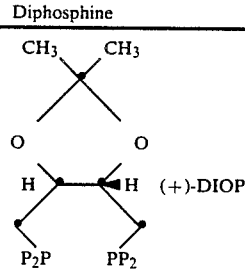 (+)-DIOP | 20 | methanol benzene (1:1) | 100 | 96 | 68(S) |
| 2 | (+)-DIOP | 20 | methanol benzene (1:1) | 48 | 72 | 60.5(S) |
| 3 | (+)-DIOP | 20 | methanol/ benzene (1:1) | 18 | 93 | 38(S) |
| 4 | 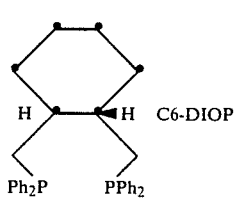 C6-DIOP | 25 | methanol/ benzene (1:1) | 43 | 30 | 28(R) |

TABLE 1-continued

| Example | Diphosphine | | Temperature (°C) | Solvent | Reaction time (hours) | Conversion (%) | Optical yield % ee (configuration) |
|---|---|---|---|---|---|---|---|
| 5 | [structure] | PPh₂ BPPM, N–O=CO-t-Butyl | 20 | methanol/benzene (1:1) | 22 | 93 | 56(S) |
| 6 | BPPM | | 20 | Tetrahydrofuran | 22 | 99 | 73(S) |
| 7 | [structure with CH₃, Ph₂P, PPh₂] | PROPHOS | 50 | methanol/benzene (1:1) | 65 | 53 | 19(S) |
| 8 | [structure with CH₃, CH₃, Ph₂P, PPh₂] | CHIRAPHOS | 50 | methanol/benzene (1:1) | 24 | 54 | 37(S) |
| 9 | [structure] | PPh₂ (+)-NORPHOS, PPh₂ | 18 | CH₂Cl | 65 | 99 | 54(R) |
| 10 | [structure with PPh₂ PPh₂] | DEGUPHOS, N–Benzyl | 50 | methanol/benzene (1:1) | 20 | 77 | 33(R) |

EXAMPLE 11–14

The procedure is as in Examples 3–10 and the reaction conditions are changed. N(2-Methyl-6-ethylphen-1-yl)-methyl-methoxymethyl-ketimine is used as the ketimine. (−)-DIOP (Example 11) and (+)-DIOP (Examples 12–14) are used as the diphosphine. The hydrogen pressure is $2 \times 10^6$ Pa. The results are shown in Table 2.

TABLE 2

| Example | Additive (equivalents per iridium) | Temperature (°C.) | Solvent | Reaction time (hours) | Conversion (%) | Optical yield % ee (configuration) |
|---|---|---|---|---|---|---|
| 11 | KI (1) | 50 | methanol/benzene | 22.5 | 90 | 49 (R) |
| 12[1] | tetrabutylammonium iodide (2) | 18 | methanol/benzene | 20 | 91 | 58 (S) |
| 13 | tetrabutylammonium iodide (2) | 18 | tetrahydrofuran | 20.5 | 98 | 61 (S) |
| 14 | tetrabutylammonium iodide (2) | 18 | ethanol | 20 | 97 | 53 (S) |

[1] 80 mmol of ketimine

EXAMPLES 15–23

The procedure is as in Examples 3–10, using various ketimines. Methylene chloride is used as the solvent in Examples 23, and otherwise benzene/methanol is used. The results are shown in Table 3.

TABLE 3

Ketimine structure:

$R^1$, $R^2$ on benzene ring ortho positions; $N=C(R^3)(CH_3)$

| Example | Ketimine | Diphosphine | Addition* (equivalents per iridium) | Reaction time (hours) | Conversion (%) | Optical yield % ee (Configuration) |
|---|---|---|---|---|---|---|
| 15 | $R^1 = R^2 = H$, $R^3 = n\text{-}C_3H_7$ | (−)-DIOP | — | 19 | 99 | 6 |
| 16 | $R^1 = R^2 = H$, $R^3 =$ Phenyl | (+)-DIOP | 2 | 18 | 90 | 22 |
| 17 | $R^1 = R^2 = H$, $R^3 =$ Phenyl | BPPM | 2 | 17 | 65 | 9.5 |
| 18 | $R^1 = R^2 = H$, $R^3 =$ Benzyl | (+)-DIOP | 2 | 19,5 | 99 | 30 |
| 19 | $R^1 = R^2 = CH_3$, $R^3 = n\text{-}C_3H_7$ | (+)-DIOP | 2 | 17 | 65 | 52 |
| 20 | $R^1 = R^2 = CH_3$, $R^3 = n\text{-}C_3H_7$ | DEGUPHOS | 2 | 42 | 62 | 1 |
| 21 | o-tolyl-N=C(CH_3)(C(CH_3)=CH_2) type imine | (+)-DIOP | 2 | 7 | 99 | 66 |
| 22 | o-OCH_3-phenyl-N=C(CH_3)(Phenyl) | (+)-DIOP | 2 | 20 | 99 | 30 |
| 23 | o-OCH_3-phenyl-N=C(CH_3)(CH_2OCH_3) | (+)-DIOP | 2 | 6 | 99 | 7 |
| 23a | 3-methyl-2-thienyl-N=C(CH_3)(CH_2OCH_3) | (+)-DIOP | 2 | 4 | 97 | 57 |

*tetrabutylammonium iodide (TBAI)

EXAMPLES 24–40

The procedure is as in Examples 3–10. The reaction conditions and results are shown in Table 4.

TABLE 4

| Example | Diphosphine | Additive (equivalent per iridium) | Pressure ($10^6$ Pa) | Temperature (°C.) | Solvent | Reaction time (hours) | Conversion (%) | Optical yield % ee (configuration) |
|---|---|---|---|---|---|---|---|---|
| 24 | (+)-DIOP | KI (1) | 2 | 18 | methanol/benzene | 66 | 98 | 62.5 (S) |
| 25 | (+)-DIOP | KI (2) | 2 | 18 | methanol/benzene | 16 | 98 | 63 (S) |
| 26 | (+)-DIOP | KI (5) | 2 | 18 | methanol/benzene | 18 | 96 | 62.5 (S) |
| 27 | (+)-DIOP | KI (10) | 2 | 18 | methanol/benzene | 38 | 100 | 65 (S) |
| 28 | (+)-DIOP | KI (20) | 2 | 18 | methanol/benzene | 42.5 | 88 | 60.5 (S) |
| 29 | (+)-DIOP | — | 2 | 18 | ethanol | 19 | 97 | 55 (S) |
| 30 | (+)-DIOP | — | 2 | 18 | benzene | 23 | 88 | 65 (S) |
| 31 | (+)-DIOP | — | 2 | 18 | tetrahydrofuran | 18 | 97 | 68.5 (S) |

TABLE 4-continued

| Example | Diphosphine | Additive (equivalent per iridium) | Pressure (10^6 Pa) | Temperature (°C.) | Solvent | Reaction time (hours) | Conversion (%) | Optical yield % ee (configuration) |
|---|---|---|---|---|---|---|---|---|
| 32 | (+)-DIOP | — | 2 | 18 | CH$_2$Cl$_2$ | 18 | 98 | 44 (S) |
| 33 | (+)-DIOP | — | 1 | 18 | methanol/benzene | 5 | 42 | 57 (S) |
| 34 | (+)-DIOP | — | 1 | 18 | methanol/benzene | 20 | 89 | 57 (S) |
| 35 | (+)-DIOP | — | 1 | 25 | methanol/benzene | 42 | 94 | 52 (S) |
| 36 | (+)-DIOP | — | 1 | 50 | methanol/benzene | 22 | 67 | 47 (S) |
| 37 | (+)-NORPHOS | — | 2 | 50 | methanol/benzene | 66 | 60 | 27 (R) |
| 38 | (+)-NORPHOS | — | 2 | 18 | methanol/benzene | 41 | 77 | 52.5 (R) |
| 39 | DEGUPHOS | — | 2 | 18 | CH$_2$Cl$_2$ | 19 | 98 | 41.5 (R) |
| 40 | (+)-DIOP | — | 2 | 25 | methanol/benzene | 17 | 96 | 39.5 (S) |

EXAMPLE 41

The procedure is as in Examples 3-10, but using 1—O—phenyl-4,6—O—(R)-benzylidene-2,3—O—bis(-diphenyl-phosphino)-β-D-glucopyranoside, 2 equivalents of TBAI per iridium and N-(2-methyl-6-ethylphen-1-yl)-methyl-methoxmethylketimine. The reaction time is 21.5 hours. At a conversion of 67%, the enantiomer excess (ee) is 44% (S).

EXAMPLE 42:

The procedure is according to the reaction conditions of Example 3 and the ketimine is produced in situ from 40 mmol of 2,6-dimethylaniline and 40 mmol of methoxyacetone. Tetrahydrofuran is used as the solvent. The reaction time is 144 hours. At a conversion of 37%, an enantiomer excess of 64% ee (S) is achieved.

What is claimed is:

1. A process for the preparation of an optically active seconday N-arylamine of the formula I

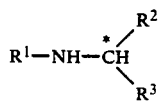

(I)

in which R$^1$ is C$_6$-C$_{12}$-aryl or C$_4$-C$_{11}$-heteroaryl which has 1 or 2 heteroatoms in the ring and is bonded via a ring C atom, it being possible for these radicals to be substituted by C$_1$-C$_{12}$-alkyl, C$_1$-C$_{12}$-alkoxy, C$_1$-C$_{12}$alkylthio, C$_1$-C$_6$-haloalkyl, halogen, —OH, —CN, C$_6$-C$_{12}$-aryl or -aryloxy or -arylthio, C$_7$-C$_{16}$-aralkyl or -aralkoxy or -aralkylthio, it being possible for the aryl radicals in turn to be substituted by C$_1$-C$_4$-alkyl, -alkoxy, -alkylthio, halogen, —OH, —CN, —CONR$^4$R$^5$ or —COOR$^4$, secondary amino with 2 to 24 C atoms,

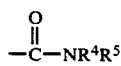

or —COOR$^4$, in which R$^4$ and R$^5$ independently of one another are C$_1$-C$_{12}$-alkyl, phenyl or benzyl or R$^4$ and R$^5$ together are tetra- or pentamethylene or 3-oxapentylene; R$^2$ and R$^3$ differ from one another and are C$_1$-C$_{12}$-alkyl or cycloalkyl with 3-8 ring C atoms, which are unsubstituted or substituted by —OH, —CN, halogen, C$_1$-C$_{12}$-alkoxy, phenoxy, benzyloxy, secondary amino with 2 to 24 C atoms,

or —COOR$^4$, C$_6$-C$_{12}$-aryl or C$_7$-C$_{16}$-aralkyl which is unsubstituted or substituted in the same way as R$^1$, —CONR$^4$R$^5$ or —COOR$^4$, in which R$^4$ and R$^5$ are as defined above; or R$^1$ is as defined above and R$^2$ and R$^3$ together are alkylene which has 2 to 5 C atoms and is uninterrupted or interrupted by 1 or 2 —O—, —S—or —NR$^4$- and/or is unsubstituted or substituted by =O or as described above for R$^2$ and R$^3$ alkyl, and/or is fused with benzene, furan, thiophene or pyrrole, or R$^2$ is as defined above, R$^1$ is bounded to R$^3$ and are alkylene which has 2 to 5 C atoms and is uninterrupted or interrupted by 1 or 2 —O—, S—or —NR$^4$- and/or unsubstituted or substituted by =O or as described above for alkyl R$^2$ and R$^3$, and/or is fused to benzene, furan, thiophene or pyrrole, and * is chiefly the R- or S-configuration, by asymmetrically catalyzed hydrogenation of an N-arylated prochiral ketimine

(II)

in which R$^1$, R$^2$ and R$^3$ are as defined above, in the presence of a complex salt of a noble metal with chiral ligands, which comprises carrying out the hydrogenation at a temperature of —20° to 80° C. under a hydrogen pressure of 10$^5$ Pa to 6.10$^6$ Pa and adding to the reaction mixture catalytic amounts of an iridium compound of the formula III or IIIa

(III)

or

(IIIa)

in which X is two olefin ligands or one diene ligand, Y is a chiral diphosphine, the secondary phosphine groups of which are linked by 2-4 C atoms and which, together with the Ir atom, forms a 5-, 6- or 7-ring, or Y is a chiral diphosphinite, the phosphinite groups of which are linked via 2 C atoms and which together with the Ir atom forms a 7-ring, Z is Cl, Br or I and A⊖ is the anion of an oxygen acid or complex acid.

2. The process according to claim 1, wherein the reaction temperature is —20° to 50° C.

3. The process according to claim 1, wherein the hydrogen pressure is 2.10$^5$ Pa to 3.10$^6$ Pa.

4. The process according to claim 1 wherein X in the formulae III and IIIa is two ethylene or one open-chain or cyclic diene, the diene groups of which are linked via 1 or 2 C atoms.

5. The process according to claim 4, wherein the diene is hexadiene, norbornadiene or cyclooctadiene.

6. The process according to claim 1, wherein Y in the formulae III and IIIa is a chiral diphosphine, the phosphine groups of which are linked by 4 C atoms and which together with the Ir atom forms a 7-ring.

7. The process according to claim 1, wherein the phosphine groups contain $C_1$–$C_{12}$-alkyl, cycloalkyl which has 5 to 8 ring C atoms and can be substituted by 1 to 3 $C_1$–$C_6$-alkyl groups, phenyl, $C_7$–$C_{12}$-phenylalkyl or alkylphenylalkyl with 1 to 6 C atoms in the alkyl groups and 1 to 5 C atoms in the alkylene group.

8. The process according to claim 1, wherein $A\ominus$ is $ClO_4$, $CF_3SO_3\ominus$, $BF_4\ominus$, $B(phenyl)_4\ominus$, $PF_6\ominus$, $SbCl_6\ominus$, $AsF_6\ominus$ or $SbF_6\ominus$.

9. The process according to claim 1, wherein the iridium compound is added in an amount of 0.01 to 5 mol %, based on the compound of the formula II.

10. The process according to claim 1, wherein an ammonium or alkali metal chloride, bromide or iodide is additionally added.

11. The process according to claim 1, wherein, in formula III, X is cyclooctadiene, Z is Cl and Y is (R)- or (S)-

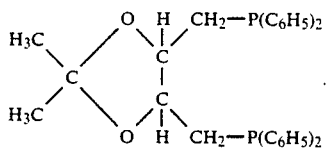

12. The process according to claim 1, wherein, in formula II, $R^1$ is 2,6-dimethylphen-1-yl or 2-methyl-6-ethylphen-1yl, $R^2$ is methyl and $R^3$ is methoxymethyl.

13. The process according to claim 1, wherein the diphosphonite is 1-O-phenyl-4,6-O-(R)-benzylidene-2,3-O-bis(diphenylphosphino)-β-D-glycopyranoside.

* * * * *